United States Patent [19]

Iwamoto et al.

[11] 4,330,775
[45] May 18, 1982

[54] APPARATUS FOR INSPECTING DEFECTS IN A PERIODIC PATTERN

[75] Inventors: Akito Iwamoto, Kamakura; Hidekazu Sekizawa, Kawasaki, both of Japan

[73] Assignee: Tokyo Shibaura Denki Kabushiki Kaisha, Kawasaki, Japan

[21] Appl. No.: 130,370

[22] Filed: Mar. 14, 1980

[30] Foreign Application Priority Data

Mar. 19, 1979 [JP] Japan ................ 54-31020

[51] Int. Cl.$^3$ ............................ G01N 21/32
[52] U.S. Cl. .................. 340/146.3 P; 350/162 SF; 356/71; 356/237
[58] Field of Search .............. 340/146.3 P; 250/550, 250/562, 572; 350/162 SF; 356/71, 237, 430; 358/106; 364/507

[56] References Cited

U.S. PATENT DOCUMENTS

| | | | |
|---|---|---|---|
| 3,614,232 | 10/1971 | Mathisen | 356/71 |
| 3,658,420 | 4/1972 | Axelrod | 356/71 |
| 3,783,296 | 1/1974 | Blevins | 250/550 |
| 3,790,280 | 2/1974 | Heinz et al. | 356/71 |
| 3,972,616 | 8/1976 | Minami et al. | 356/71 |
| 3,989,387 | 11/1976 | Hategan | 250/572 |
| 4,000,949 | 1/1977 | Watkins | 350/162 SF |
| 4,118,107 | 10/1978 | Parrent et al. | 350/162 SF |
| 4,159,164 | 6/1979 | Dammann et al. | 350/162 SF |
| 4,197,011 | 4/1980 | Hudson | 250/550 |

OTHER PUBLICATIONS

Watkins, "Inspection of I.C. Photomasks With Intensity Spatial Filters", Proc. of the IEEE, vol. 57, No. 9, Sep. 1969, pp. 1634-1639.
Will et al., "Filtering of Defects in I.C. With Orientation Independence", Applied Optics, vol. 10, No. 9, Sep. 1971, pp. 2097-2100.
Flamholz et al., "Dimensional Measurement and Defect Detection Using Spatial Filtering", IBM Journal of R. & D., Nov. 1973, pp. 509-518.

Primary Examiner—Leo H. Boudreau
Attorney, Agent, or Firm—Oblon, Fisher, Spivak, McClelland & Maier

[57] ABSTRACT

An apparatus for inspecting a defect in a periodic pattern on an object is provided with a laser device for projecting a laser beam toward the object. A mechanism further included in the defect inspecting apparatus rotates the object in a plane orthogonal to an optical path of the laser beam while moving in the same plane. A spatial band-pass filter is located at the backward focal plane of a lens for Fourier-transforming the laser beam including the information of the periodic pattern and a defect, the laser beam coming from the object. The band-pass filter has a spot-like area for blocking the zeroth order diffraction light transmitted through the periodic pattern a peripheral light blocking area for blocking the first and higher order diffracted light beams, and a ring-like light transmission area permitting the light beam component including the information of a defect to pass therethrough, the light transmission area being located between the spot-like area and the peripheral area. A photo-electric converter for picking up the light beam component including the defect information transmitted through the filter is located on an image forming plane where an image of the object is formed by a lens.

11 Claims, 18 Drawing Figures

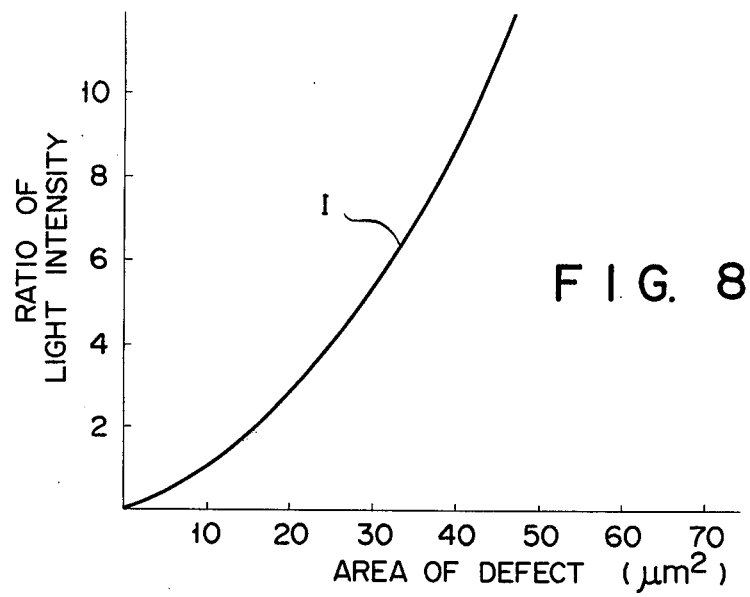
FIG. 8
FIG. 9
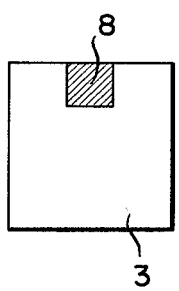
FIG. 10
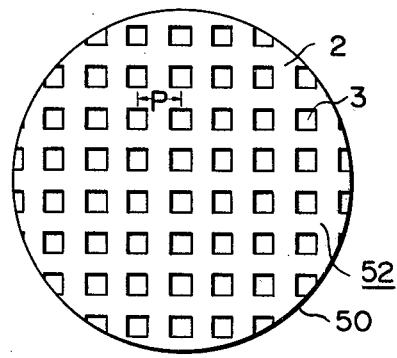

F I G. 18
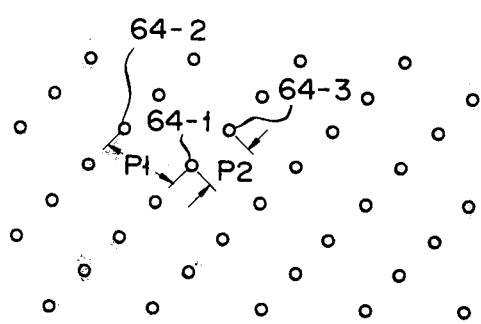

APPARATUS FOR INSPECTING DEFECTS IN A PERIODIC PATTERN

This invention relates to an apparatus for inspecting or finding defects in a periodic pattern.

In a conventional apparatus for inspecting defects in a periodic pattern, the pattern is visually examined by using a microscope. Because of the visual examination, the conventional apparatus is inherently accompanied by inaccuracy of the examining result. To avoid this problem, some proposals have been made employing the combination of coherent light rays and a spatial filter. One of the proposals separates the optical information of the periodic pattern into the periodic pattern information and the non-periodic pattern information representing the defect. This type proposals are disclosed in Proceeding of IEEE, Vol. 57, No. 9, September 1969, pp. 1634 to 1639, "Inspection of Integrated Circuit Photomasks with Intensity Spatial Filters" by Watkins and in a paper entitled "Inspection of Mesh defects with Spatial Filters" by Morita et al pp. 135 to 136, Conference Record of Spring Meeting of The Japan Society of Precision Engineering in 1974 (in Japan). The proposals in those papers each employs a spatial filter which blocks the transmission of the Fourier transformed images of the normal periodic pattern periodically distributed while it permits the non-periodic pattern information to be transmitted therethrough. As seen from the papers, the following conditions are required for the proposals:

(1) The spatial filter and a pattern to be examined must be precisely aligned with each other in orientation.
(2) A lens as a Fourier transformer must be of a high precision type with little distortion.
(3) The pattern must be positioned with respect to an optical axis of an optical system in the inspection apparatus with an extremely high precision.

Those requirements result in enlargement of the apparatus size and expense, and restriction of the inspection speed.

There is another approach which is directed to the inspection of a disc-like pattern by using a spatial band-pass filter and by which apertures larger or smaller than a specific size are detected as defects with high precision, as disclosed by A. L. Flamholz and H. A. Froot; IBM J. RES. DEVELOP "Dimensional Measurement and Defect Detection" pp. 509 to 518, November 1973 as quoted in the literature. This approach, however, requires the following conditions:

(1) When the shape of apertures is not circular, the pattern to be examined and the spatial filter must be aligned with each other in the orientation.
(2) The spatial filter used must be of a high precision type and must be positioned accurately.
(3) The pattern to be examined must be held accurately orthogonal to an optical axis of the optical system of the inspection apparatus.

Those requirements make the defect inspection apparatus complicated in the mechanism and high in cost.

Accordingly, an object of the invention is to provide an apparatus for inspecting defects in a periodic pattern which has a relatively large allowance of the relative positioning and orientation of a periodic pattern and optical elements in an optical system of the apparatus and can find a defect or defects of the periodic pattern at a high speed.

According to the invention, there is provided an apparatus for inspecting defects in a periodic pattern comprising; means for forming a Fourier transformed pattern of the periodic pattern and filtering means for passing predetermined spatial frequency ranges of the Fourier transformed pattern, the predetermined spatial frequency ranges being between a first spatial frequency which coincides with a zero order diffraction of the Fourier transformed pattern and a second spatial frequency which coincides with a first order diffraction of the Fourier transformed pattern.

Other objects and features of the invention will be apparent from the following description taken in connection with the drawings, in which:

FIG. 8 shows a relation between an area of a defect and an electric signal obtained from a photo-electric converter used in the apparatus shown in FIG. 7;

FIG. 9 is a plan view of a square hole with a defect in a periodic pattern, which is used for describing a graph shown in FIG. 8;

FIG. 10 is a plan view of a periodic hole pattern of a mesh plate inspected by the defect inspection apparatus in FIG. 7;

FIG. 18 illustrates another example of the periodic pattern.

In the specification, a term "defect" means factors to distort a periodic pattern such as a different size of the pattern, a deformation of the pattern, scratches of the pattern, and dust stuck to the pattern. The defect inspection apparatus according to the invention is used to detect such defects in the periodic pattern.

By way of example, a mesh plate with a mesh pattern assembled into a vidicon or shadow mask for a color cathode ray tube is used as an object with a periodic pattern to be inspected in the specification. Such an object, however, is not limited to the mesh plate but may be an opaque object with a periodic pattern, for example, semiconductor products, as will be described later.

Before proceeding with a description of an embodiment of the defect inspection apparatus according to the invention, a basic concept of the invention will be described referring to FIGS. 1 to 6.

Figure 1:
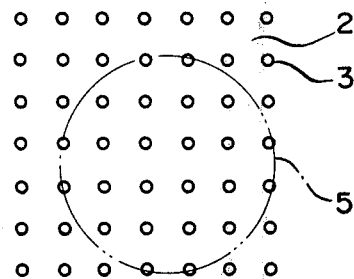
FIG. 1 shows a plan view of a mesh plate with a number of circular holes as an example of a periodic pattern, which is useful in explaining a basic theory of an apparatus for inspecting defects in a periodic pattern according to the invention.
Figure 2:
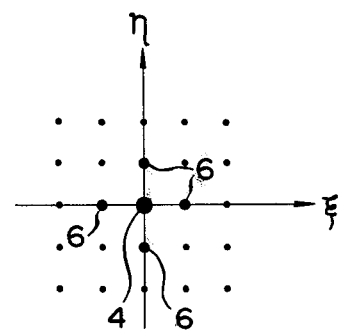
FIG. 2 is a plan view of a diffraction pattern obtained by Fourier-transforming the periodic pattern shown in FIG. 1.
Figure 3:
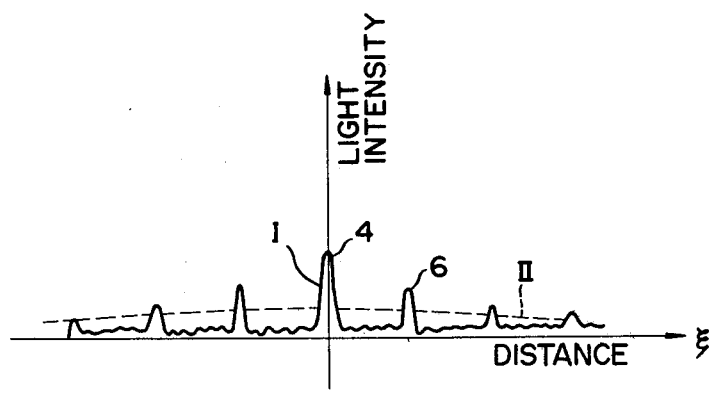
FIG. 3 shows a diffraction light intensity distribution of the image shown in FIG. 2.
Figure 4:
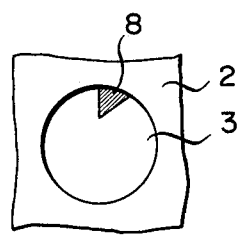
FIG. 4 shows an enlargement of one of the holes in the mesh plate which has a defect.

In FIG. 1, there is shown a mesh plate 2 with a number of periodically arranged holes 3. When a coherent light beam 5 impinges upon the mesh plate 2 with the holes 3, the light beam from the pattern being Fourier-transformed by a lens makes a diffraction pattern at the back focal plane of the lens as shown in FIG. 2. As seen from FIG. 2 illustrating the diffraction pattern with the orthogonal coordinate system having $\xi$ and $\eta$ axes, a zeroth order diffraction light component is directed to the origin area 4, a first order diffraction light is directed to an outside area 6 of the zeroth order area, and second and higher order diffraction light are similarly directed to a further outside area of the first order diffraction area. The light intensity distribution of those diffraction light on the $\xi$ axis is generally illustrated by a continuous solid line I in FIG. 3. The diffraction patterns as shown in FIG. 2 and FIG. 3 is periodic and is determined by the hole pattern in the mesh plate 2. If one of the holes 3 has a defect 8 as shown in FIG. 4, whose diffracted light intensity distribution pattern is indicated by a broken line II in FIG. 3, the total diffracted pattern is given by the pattern I added by the pattern II in FIG. 3. Therefore, if a spatial filter to filter out the periodic diffraction pattern in FIG. 2 is used, the non-periodic pattern representing the defect may be extracted from the diffracted pattern in FIG. 2. In other words, only the defect information may be detected.

Figure 5:
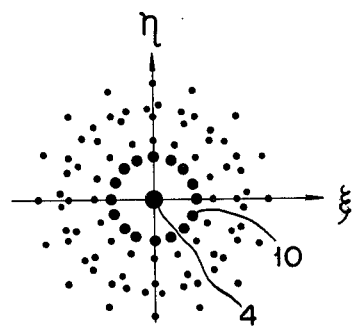
FIG. 5 is a plan view of a diffraction image pattern formed by Fourier-transforming the periodic pattern rotated with the rotation of the mesh plate shown in FIG. 1.

The technical fact mentioned above has already be described in the above-mentioned article. The invention takes advantage of a nature of the diffraction pattern obtained when the mesh plate 2 in FIG. 2 is rotated. When the mesh plate 2 is rotated, a coherent light beam projected onto the rotating mesh plate 2 and transmitted through the mesh plate 2 makes a mesh plate diffraction pattern as shown in FIG. 5 at the infinity in case without using of the lens or at the back focal plane of the lens. In FIG. 5, a number of spots coaxially distributed with respect to the origin of the orthogonal coordinates system are plotted; however, those spots in fact are distributed with a number of rings arranged coaxially with respect to the origin of the coordinates, as easily seen from the figure. Comparing with the diffraction areas, the zeroth order diffraction area 4 is formed at the origin as a spot. The first order diffraction area 10 changes as a ring around the zeroth order diffraction area. The second and higher order diffraction area similarly change as rings outside the first order diffraction area. Little light which is transmitted through the periodic hole pattern is diffracted into a space between the zeroth order diffraction area 6 like a spot and the first order diffraction area 10, even when the mesh plate 2 rotates. Accordingly, by projecting the Fourier-transformed light onto a band-pass filter 12, shown in FIG. 6, with a ring like light-transmission area like the diffraction pattern shown in FIG. 5, the periodic pattern is blocked but only the non-periodic pattern including the defect information is allowed therethrough. In the band-pass filter 12 shown in FIG. 6, a hatched area 15 blocks the transmission of the light and a blank area 13 permits the light beam to transmit therethrough. In the present invention, the mesh plate 2 may be moved laterally to an optical axis of an optical system of the apparatus, in addition to the rotation of the mesh plate 2. So long as the light beam path and the diameter of the light beam incident upon the mesh plate 2 are not changed, the diffraction pattern as shown in FIG. 5 occurs at the same location. This is true for a case where the center of the mesh plate 2, about which the mesh plate 2 rotates, is shifted with the movement of the mesh plate 2. Accordingly, the diffraction pattern remains unchanged. The reason for this is that the light information after passing through the mesh plate 2 always includes the pattern information with the unchanged number of holes and the shapes of the holes are identical with each other. Consequently, if the mesh plate 2 is moved while being rotated, it is possible to separate the light information into the periodic pattern information and the non-periodic pattern information. Therefore, the defect inspection apparatus according to the invention based on such a technical concept enables the defect inspection or finding to be performed at a high speed with a rough alignment of the periodic pattern with the optical filter in its orientation. Particularly, the later feature simplifies the defect inspection apparatus per se in the construction.

An embodiment of the defect inspection apparatus according to the invention will be described referring to FIGS. 7 to 15.

Figure 7:
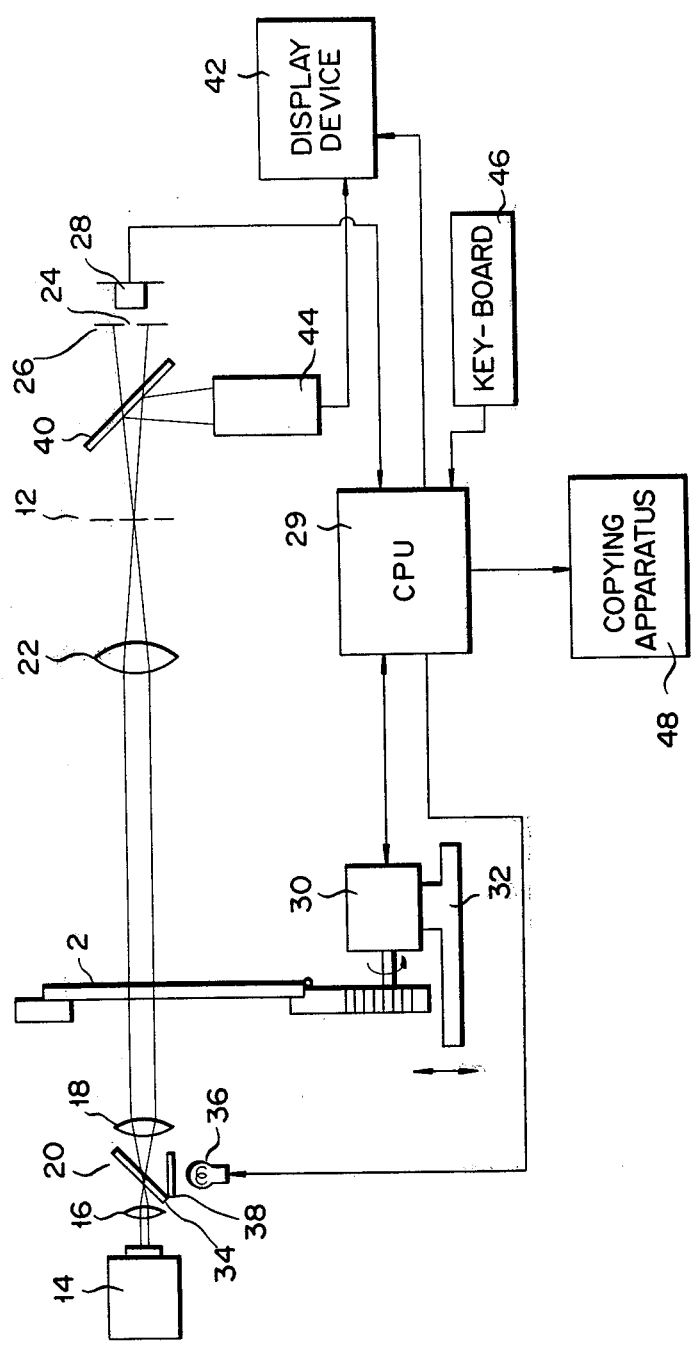
FIG. 7 is a schematic diagram of the defect inspection apparatus of the invention.

In FIG. 7 illustrating the apparatus for inspecting or finding a defect or defects of a periodic pattern on an object, a collimator 20 including lenses 16 and 18 is disposed on an optical path of a coherent light beam emitted from a light source 14 such as a laser device for generating a coherent light beam with a single wavelength. The collimator 20 converts the coherent light beam into a parallel pencil of light rays. A mesh plate with a number of holes of an identical shape arranged periodically thereon, which is inspected, is disposed on the optical path of the parallel light beams. A lens 22 disposed on the light path of the parallel light beam transmitted through the mesh plate 2 Fourier-transforms the light beam. A band-pass spatial filter 12 is located at a backward focal point of the lens 22 at which the Fourier-transformed pattern of the periodic hole pattern is formed. As previously mentioned, the laser beam transmitted through the mesh plate 2 includes the information of the periodic hole pattern and the information of the defect. The periodic hole pattern information is eliminated by the filter 12 while only the defect information is allowed to pass therethrough. A defect information detector 30 for detecting a position and size of the defect is disposed back of the filter 12. The detector includes a screen 26 with a pinhole 24 positioned at the optical path of the optical system, and a photo-electric converter 28 which is located at the back of the screen 26 and have a light sensing surface faced to the pinhole 24. The screen 26 is disposed on an image forming plane determined by the mesh plate 2 and the lens 22. If the band-pass filter 12 is not located on the optical path, a mesh pattern image of the mesh plate 2 is formed on the screen, as known. Conversely, if the filter 12 is located thereon, it allows only the defect information to pass therethrough, so that a beam spot is formed on the screen 26 at a position corresponding to the position of the defect on the mesh plate 2 by the light beams including the defect information. If the pinhole 24 is provided at the predetermined position where the beam spot is formed, the photo-electric converter 28 picks up a light intensity corresponding to the size of the defect. The photo-electric converter 28 supplies the output signal to a CPU 29, for example a micro computer. The size of the defect may easily be calculated from the output signal by the CPU 29. The output signal from the converter 28 depends on the defect size as shown in FIG. 8. A graph I shown in FIG. 8 illustrates a relation of the magnitude of the output signal (expressed by a ratio of the light intensity defined below) vs. a size or area of the defect. In plotting the graph, each hole 3 of a periodic hole pattern is a square configuration of 9 $\mu$m $\times$ 9 $\mu$m and a defect 8 of the hole has an area of 1 $\mu$m$^2$, as well illustrated in FIG. 9. The light intensity of the output signal from the photo-electric converter 28 measured when it picks up an electric signal corresponding to the amount of light emanating from the defect of 1 $\mu$m$^2$, is defined as 1, plotted along the ordinate axis of the graph. As seen from the graph, there is a definite relation between the magnitude of the defected signal and the size of the defect. Accordingly, the size of the defect may be evaluated from the magnitude of the detected signal.

The mesh plate 2 is supported by a rotating mechanism 30 to rotate the mesh plate 2 in a plane normal to the optical axis of the optical system. The rotating mechanism 30 is further supported by a moving mechanism 32 to move the mechanism at constant rate in the rotating plane. The mesh plate 2 is laterally moved while being rotated by means of those mechanisms, so that the mesh plate 2 is helically scanned by the coherent parallel light beams emanating from the collimator 20. A stopping mechanism (not shown) is coupled with those rotating and moving mechanisms 30 and 32 to instantaneously stop the operation of those mechanisms when a defect is detected by the photo-electric pickup. The CPU 29 applies a stop signal to the stopping mechanism, when the level of the output signal from the photo-electric converter 28 exceeds a predetermined one, for example. Position signals relating to the amounts of displacements of the mesh plate 2 are generated at those mechanisms 30 and 32 and supplied to the CPU 29.

The collimator 20 is further provided with a dichroic mirror 34 for reflecting the light rays having a specific wavelength in order to superpose incoherent light rays on the coherent light rays projected from the laser device 14, and a light source 36 for emitting the incoherent light rays toward the dichroic mirror 34. A wavelength selection filter 38 is further disposed between the light source 36 and the dichroic mirror 34. The filter 38 allows the light rays with a specific wavelength alone to pass therethrough. The incoherent light source 36 lights up in response to an energizing signal transferred from the CPU 29. The CPU 29 produces the energizing signal when a defect of the hole pattern is found. Desirable for the wavelength selection filter 38 is a filter which allows only the light ray with a single wavelength different from that of the coherent light ray from the laser device 14 to pass therethrough. When the coherent light ray is red, for example, a filter for selecting the light ray of green may be preferably selected for the wavelength selection filter 38. In this case, the mesh pattern of the mesh plate 12 is imaged on the screen 26 by the green light rays. On the other hand, the defect is imaged on the same as a red spot. Accordingly, a mesh pattern of green and a defect spot of red appear on the screen with an excellent contrast. The defect spot is distinctly visualized in the mesh pattern image on the screen 26.

In such a case where two color light rays are projected on the mesh plate 2, the band-pass filter 12 is preferably made of material exhibiting no filtering action of the incoherent light. For example, in case where the coherent light is red and the incoherent light is green, a gelatine filter is most suitable for the spatial filter 12. However, a proper color glass filter may be used for the filter in accordance with the wavelength of the selected coherent and incoherent light rays. To clearly distinguish the defect image from the mesh pattern image, a dichroic mirror 40 for reflecting only the incoherent light rays projected from the light source 36 is disposed between the band-pass filter 12 and the screen 26. On the optical path of the light rays reflected from the dichroic mirror 40 is disposed an image pickup device 44 to supply a video signal to a display device to monitor the mesh pattern of the mesh plate 2, for example, a cathode ray tube device. The image pickup device 44 may be an industrial television tube (ITV tube). Since the image pickup device 44 is used for pick up the mesh pattern image, it is located at an image formation plane of the mesh pattern image on the optical path including the mesh plate 2, the lens 22, the band-pass filter 12 and the dichroic mirror 40, as in the case of the screen 26. The CPU 29 supplies a signal including the information relating to the size and location of the defect to the display device 42. The defect display signal supplied is combined with a mesh pattern signal from the image pickup tube 44 and the defect spot is displayed at an appropriate position in the mesh pattern image on the screen of the display device 42 with a proper size.

The CPU 29 is further coupled with a keyboard 46 through which the start and stop of the rotating and moving mechanisms 30 and 32, and the energization of the light source 36 are controlled, and a hard copying apparatus for copying the result of the processing by the CPU 29.

It will now be briefly described how to determine a shape of the filter 12 used in this invention.

Figure 11:
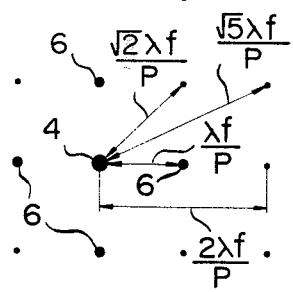
FIG. 11 shows a diffraction image pattern formed by Fourier-transforming the periodic hole pattern shown in FIG. 10.
Figure 12:
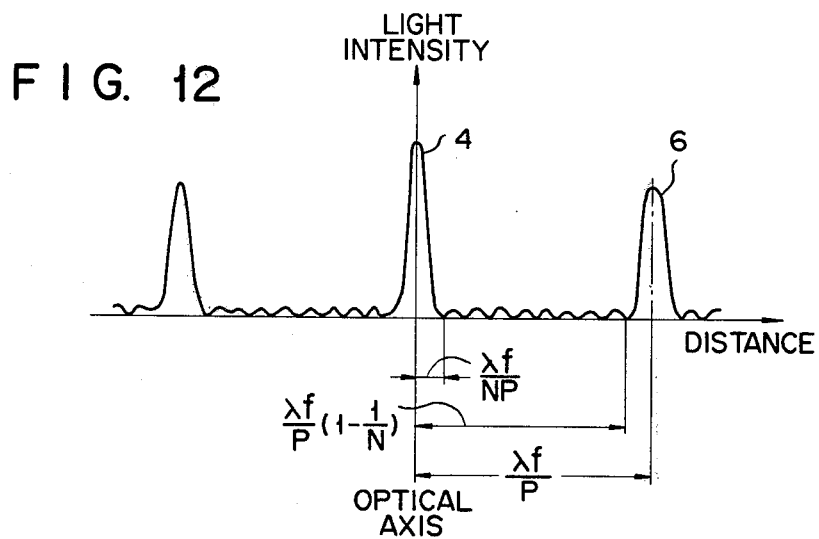
FIG. 12 illustrates a distribution of light intensity of diffraction images shown in FIG. 11.

Suppose a coherent light beam having such a size as indicated by a circle 50 is projected onto a mesh pattern 52 (i.e. the mesh plate 2 having holes 3). Let "P" denote the pitch of the pattern 52, i.e. interval between the adjacent holes 3, and "N" denote the number of holes within the circle 50 as counted in a direction of the pitch (N=8 in FIG. 10). Then, the mesh pattern 52 will be Fourier-transformed as illustrated in FIG. 11, and the light intensity of the pattern 52 will distributed as illustrated in FIG. 12. In FIGS. 11 and 12 the zeroth order diffraction area is denoted by numeral 4, and the first order diffraction area by number 6. As clearly shown in FIG. 12, the distance between the zeroth order diffraction area 4 and the first order diffraction area 6 is $$\frac{\lambda f}{P}\left(1 - \frac{2}{N}\right),$$

where λ is the wavelength of the coherent light projected and f is the frequency of the coherent light. The diameter of diffraction area 4 is $2 \times \lambda f/NP$. The diffraction area 6 is between $$\frac{\lambda f}{P}\left(1 - \frac{1}{N}\right) \text{ and } \frac{\lambda f}{P}\left(1 + \frac{1}{N}\right).$$

Figure 6:
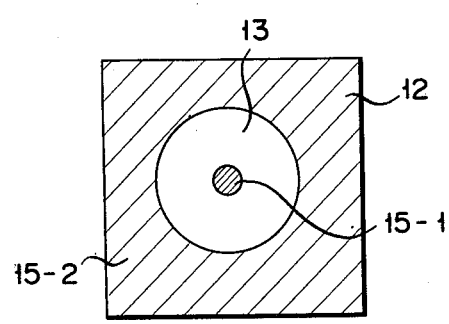
FIG. 6 is an example of a band-pass spatial filter assembled into the defect inspection apparatus according to the invention, which is designed corresponding to the diffraction image pattern shown in FIG. 5.

As shown in FIG. 6, a light block area 15-1 is within a radius of $\lambda f/NP$ from the center of the filter, another light block area 15-2 is beyond a radius of $$\frac{\lambda f}{P}\left(1 - \frac{1}{N}\right)$$

from the center of the filter, and a light transmission area 13 is provided between these light block areas 15-1 and 15-2.

Figure 13:
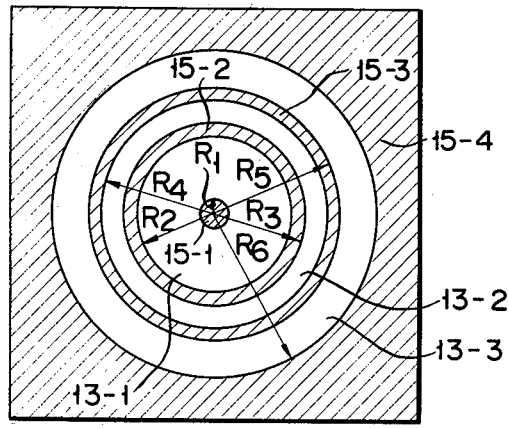
FIG. 13 shows a plan view of another example of the band-pass spatial filter assembled into another defect inspection apparatus according to the invention.

FIG. 13 shows another spatial filter which has three ring-like light transmission areas 13-1 to 13-3 and four light block areas 15-1 to 15-4. The light block area 15-1 is circular, and its center is identical with that of the filter and its radius is $\lambda f/NP(=R_1)$. The light block areas 15-2 and 15-3 are ring-shaped and concentric with the light block area 15-1, and their inner radii are $$\frac{\lambda f}{P}\left(1 - \frac{1}{N}\right) (= R_2) \text{ and } \frac{\sqrt{2}}{P}\lambda f - \frac{\lambda f}{NP} (= R_4)$$

and their outer radii are $$\frac{\lambda f}{P}\left(1 + \frac{1}{N}\right) (= R_3) \text{ and } \frac{\sqrt{2}}{P}\lambda f + \frac{\lambda f}{NP} (= R_5),$$

respectively. And the light block area 15-4 is defined by a circle which is concentric with the light block areas 15-1 to 15-3 and whose radius is $$\frac{\sqrt{5}}{P}\lambda f - \frac{\lambda f}{NP} (= R_6).$$

The light transmission area 13-1 lies between the light block areas 15-1 and 15-2, the light transmission area 13-2 between the light block areas 15-2 and 15-3, and the light transmission area 13-3 between the light block areas 15-3 and 15-4. The width of each of light block areas 15-1 to 15-4 is $2 \times \lambda f/NP$ or more. The spatial filter of FIG. 13 can more improve the sensitivity of defect detection than the spatial filter of FIG. 6 and can therefore enhance the resolution with respect to fine defects.

In operation, the mesh plate 2 is set to the rotating mechanism 30, the laser device 14 is energized, and a start instruction is entered into the CPU 29 from the keyboard 46. Upon the start initiation, the mesh plate illuminated by the laser beam is rotated while being moving laterally, so that the area of the mesh plate 2 is helically scanned by the laser beam at a high speed rate. When a defect 8 is found in the area of the periodic holes pattern on which the laser beam is projected, the CPU 29 produces a stop signal to the mechanisms 30 and 32 to stop them. At this time, the light source 36 is energized to emit the incoherent light. The periodic pattern information included in the incoherent light and transmitted through the mesh plate 2 is picked up by the image pickup device 44 and is displayed by the display device 42. The defect information included in the coherent light coming from the laser device 14 through the mesh plate 2, the lens 22, and the spatial filter 12 is picked up by the photoelectric converter 28 and is supplied to the CPU 29. The CPU 29 calculates the position of the defect and its size by using the position information from the mechanisms 30 and 32 and the defect information from the converter 28 and supplies them to the display device 42 where those are visualized. An operator checks that a defect is found in the mesh plate 2 by seeing the display and then drives the rotating and moving mechanisms 30 and 32 through the keyboard 46. When the entire area of the mesh plate 2 is helically scanned by the laser beam, the inspection of the mesh plate is completed. As the inspection is completed, the CPU 29 delivers the periodic pattern information and the defect information, which are stored in a memory, to the copying machine to copy the information.

As described above, the invention employs a spatial filter with ring-like light transmission areas, as shown in FIG. 6 or 13, the filtering by the filter is free from an angular-dependency, that is, may be made omnidirectionally. Because of the nature of the Fourier transformation employed, the filtering operation is little affected by lateral shift of the object 2 to be inspected. Accordingly, the same filtering of the pattern information is possible even if the array of the pattern, the shape of the hole, and the position of the hole are different and the pattern is rotated. Accordingly, there is no need for a precise alignment of the filter 12 with the object 2 in the orientation. Additionally, since the object 2 may be scanned helically, it is possible to inspect the entire surface of the object 2 at a high speed rate. Since the filter 12 shown in FIG. 6 shuts out all the diffraction light rays of the first order and higher order, there is eliminated a need of the alignment of the high order diffraction light rays with the filter 12. Moreover, a high accuracy is not needed for the lens 22 because the spatial filter 12 prevents the transmission of the higher degree diffraction light rays which is affected by the lens distortion. The spatial filter may also detect a defect even when the filter is set roughly and the physical accuracy of the filter is not so severe. Additionally, a severity is not required for the setting and the dimensional accuracies of the filter.

Figure 14:
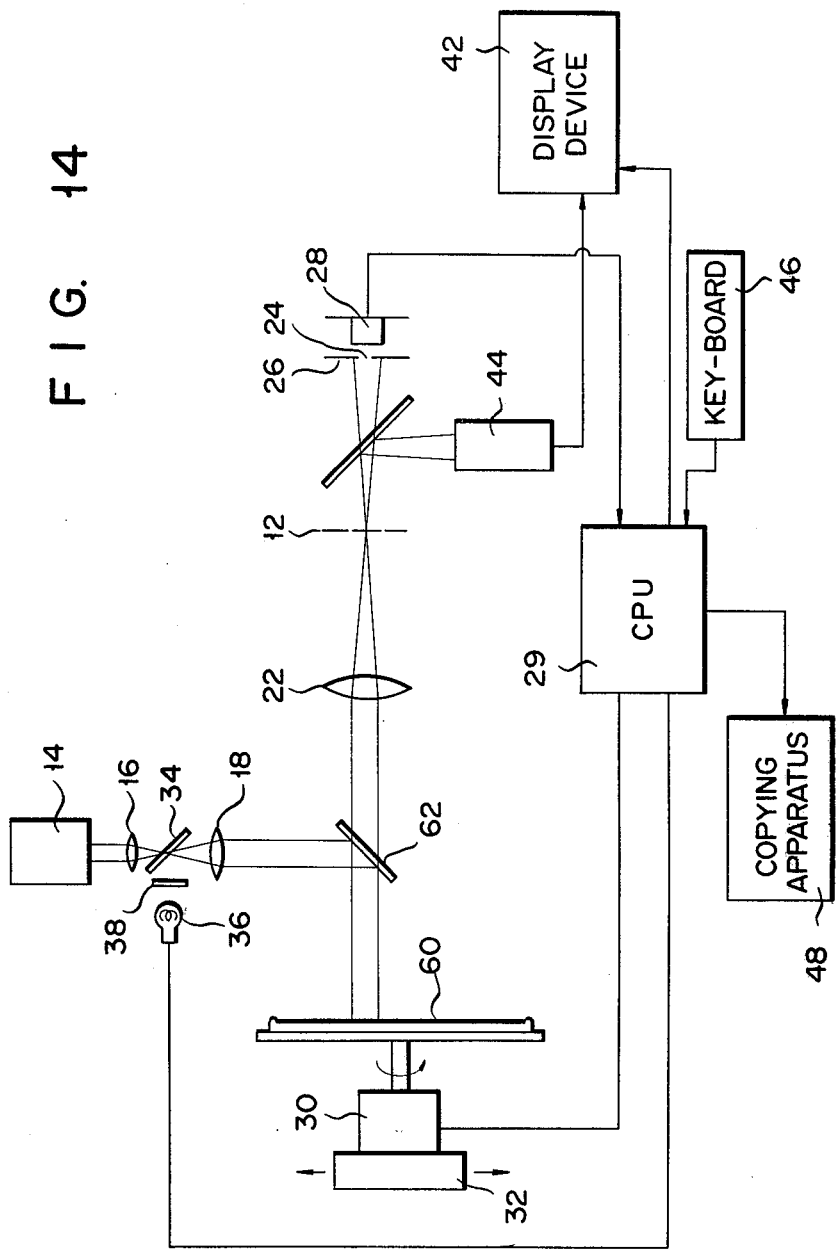
FIG. 14 shows a schematic diagram of the defect inspection apparatus according to the invention.

Turning now to FIG. 14, there is shown another embodiment of an apparatus for inspecting defects in a periodic pattern on an object of light reflecting type. Like reference numerals are used for designate like portions in FIG. 7. Because of the light reflecting nature of the periodic pattern, a semi-transparent mirror 62 is disposed between the Fourier transformer 22 and the object 60 and on the optical axis of the collimator 20, in order that the light beam reflected from the periodic pattern on the object 60 is directed toward the Fourier transformer 22.

With such a construction, even if the periodic pattern is of opaque type, a defect in the pattern may be detected.

Figure 15:
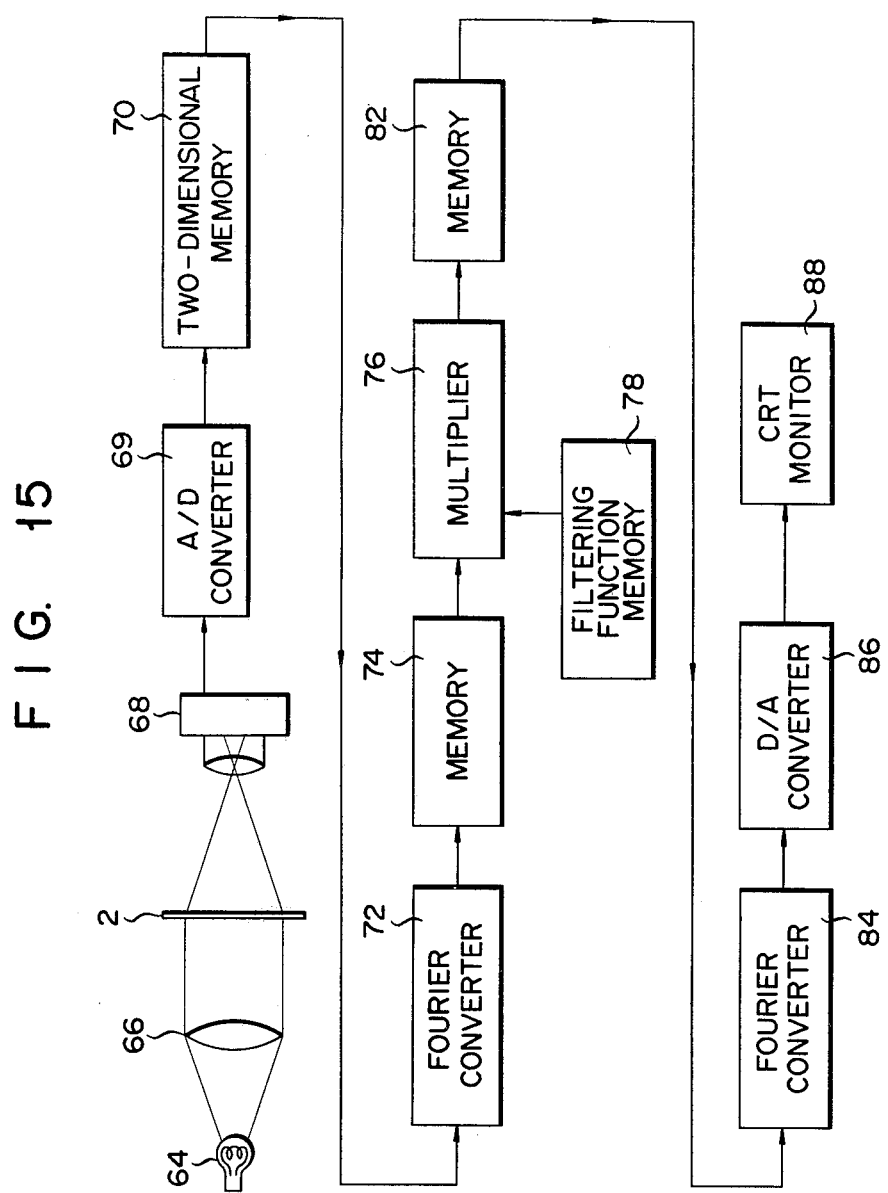
FIG. 15 shows a block diagram of the defect inspection apparatus according to the still another embodiment of the invention.
Figure 16:
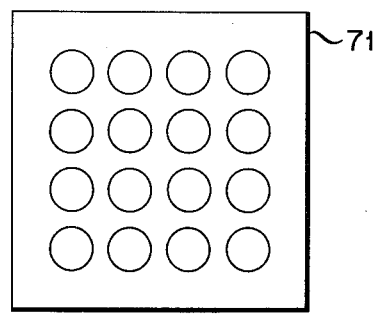
FIG. 16 shows a plan view of a periodic pattern image.

FIG. 15 shows another embodiment of this invention. Unlike the apparatus shown in FIGS. 7 and 14, the apparatus of FIG. 15 obtains information about a Fourier transform image of a periodic pattern without using an optical system and takes out defect information from the image information by arithmetic operations. Mose specifically, a light source 64 emits incoherent light, which is applied through a lens 66 onto a periodic pattern 2. The light passes through the pattern 2, thus forming a periodic pattern image 71 of such a predetermined area as shown in FIG. 16. The image 71 is sampled by an image pickup device 68 and converted into analog image signals. The analog image signals thus obtained are supplied to an analog-digital converter 69 and are converted into digital image signals. The digital image signals are stored into a two-dimensional memory 70 which can store n×n digital signals. That is, the periodic pattern image 71 is split by the image pickup device 68 into n×n pixells, the pixells are converted into digital signals, and the digital signals are stored at prescribed addresses of the memory 70.

Figure 17:
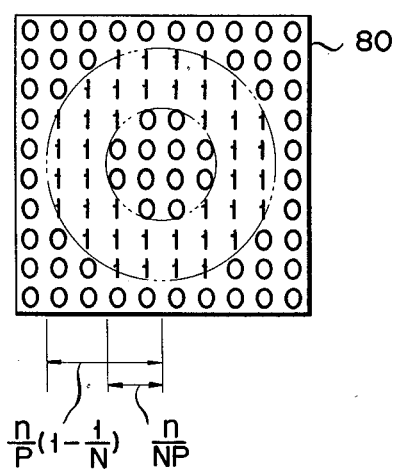
FIG. 17 shows a filtering function memory data.

The digital image signals are read out from the memory 70 and undergo Fourier transformer operation at a Fourier converter 72. The signals from the Fourier converter 72 are then stored into a two-dimensional memory 74. The Fourier converter 72 may be the AP-400 which is already put on market by ANALGIC Inc. and which achieves a high speed Fourier conversion. The signals are read out from the Fourier converter 72 and then multiplied one after another by a multiplier 76. Of these signals, only defect signals are stored into a memory 82. The multiplication at the multiplier 76 is carried out according to a filtering function data stored in a filtering function memory 78, thereby to take out only the defect signals. As shown in FIG. 17, the filtering function data consists of n×n digital data. The area filled with digit numerals "0" correspond such a light block area as illustrated in FIG. 6, and the area filled with digit numerals "1" to such a light transmission area as shown in FIG. 6. In other words, the filtering function data is a pattern formed of digital signals which correspond to n×n pixells defining the image of the band-pass spatial filter of FIG. 6. The number of pixels which corresponds to the diameter of the light block area of FIG. 6 is expressed as n/NP, whereas the number of pixels which corresponds to the width of the light transmission area of FIG. 6 is expressed as $$\frac{n}{P}\left(1 - \frac{2}{N}\right).$$

Here, n corresponds to λf which has been described above with reference to FIGS. 12 and 13.

The defect signals read out from the memory 82 are supplied to an inverse Fourier converter 84. They undergo an inverse Fourier conversion and converted into pixell digital signals which represent an defect image. The inverse Fourier converter 84 may be of the same type as the Fourier converter 72. The pixell digital signals thus obtained are supplied to a digital-analog converter 86 and thus converted into defect image signals. The defect image signals are supplied to a CRT monitor 88, whereby the defect image is displayed. The CRT monitor 88 may display not only the shape and position of the detect but also the size of the detect. The apparatus of FIG. 15, though not provided with an optical system, can detect a defect.

Although the periodic pattern shown in FIGS. 1, 10 and 16 have holes arranged equidistantly, those elements of the pattern are not necessarily arranged so. For example, as in the pattern shown in FIG. 18, the distances from the element 64-1 to the adjacent elements 64-2 and 64-3 are P1 and P2 are not equal. Such a pattern is allowable so long as the pattern is arranged periodically.

What we claim is:

1. An apparatus for inspecting defects in a periodic pattern comprising:
    a light source for producing a coherent light directed to the periodic pattern to be inspected;
    a fourier transformer for Fourier-transforming a light including the information of the periodic pattern and defects; and
    filtering means positioned at the backward focal point of the Fourier transformer and having a light block areas for blocking mainly the periodic pattern information component of the light passed the Fourier transformer and a ring-like light transmission area allowing mainly the defects information component of the light to pass therethrough, the light block area including a first light block area of spot like shape which prevents a transmission of the zeroth order diffraction light transmitted through the Fourier transformer and a second light block area which is disposed around the first area and prevents a transmission of the first and higher order diffraction light transmitted through the Fourier transformer.

2. An apparatus for inspecting defects in a periodic pattern according to claim 1, further comprising photoelectric converting means substantially positioned at an image forming plane on which the periodic pattern is imaged by said Fourier transformer and picking up the light intensity of the defect information component.

3. An apparatus for inspecting defects in a periodic pattern according to claim 1, further comprising a means for shifting the pattern in a direction orthogonal to the optical path of the coherent light beam and means for rotating the periodic pattern in a plane normal to the optical path of the coherent light.

4. An apparatus for inspecting defects in a periodic pattern according to claim 1, in which said filtering means is comprised of a first spot-like block area for blocking the zeroth order diffracted light of the light reflected from or transmitted through the periodic pattern and Fourier-transformed by said Fourier transformer, a second ring-like block area for blocking the first order diffracted light, a third ring-like light blocking area for blocking the second order diffracted light, a fourth light blocking area for blocking the third and higher order diffracted light and first to third ring-like light transmission areas each located between the adjacent light blocking areas.

5. An apparatus for inspecting defects in a periodic pattern according to claim 1, in which, when the periodic pattern is a mesh like configuration which is light transmission type.

6. An apparatus for inspecting defects in a periodic pattern according to claim 1, in which, the periodic pattern is a light reflective type.

7. An apparatus for inspecting defects in a periodic pattern according to claim 1, further comprising an incoherent light with a wavelength different from that of the coherent light generated from the coherent light source, and means for superposing the incoherent light on the optical path of the coherent light and is directed to the periodic pattern.

8. An apparatus for inspecting defects in a periodic pattern according to claim 2, further comprising means for analyzing the size of a defect on the basis of the light intensity picked up by the photo-electric converting means.

9. An apparatus for inspecting defects in periodic pattern according to claim 2, comprising means for shifting the periodic pattern in a direction orthogonal to the optical path of the coherent light, means for rotating the periodic pattern in a plane normal to the optical path of the coherent light and means for analyzing the position of the defect on the basis of the output signal from the photo-electric converting means and number of revolutions of the rotating means and an amount of the movement of the shifting means.

10. An apparatus for inspecting defects in a periodic pattern according to claim 7, further comprising means for displaying an image of the periodic pattern which is formed on an image forming plane of the incoherent light reflected from or transmitted through the periodic pattern and Fourier transformed.

11. An apparatus for inspecting defects in a periodic pattern, comprising:

means for converting an image of a periodic pattern to be inspected into digital signals including defect signals and periodic pattern signals;

means for fourier-transforming the digital signals from said converting means;

filter means having a memory storing pattern data for processing the digital signals according to the pattern data, thus filtering only the defect signals included in the digital signals, said pattern data each consisting of a block area data for blocking periodic pattern information and a ring-like area data for transmitting defect information, said block area data containing a first area corresponding to a first-order diffraction image formed by fourier-transforming the image of the periodic pattern and a second area data corresponding to a higher-order diffraction image;

means for inversely fourier-transforming the defect signals from the filter means; and means for displaying defects according to the defect signals from said inverse fourier-transforming means.

* * * * *